(12) United States Patent
Stürmer et al.

(10) Patent No.: US 6,359,165 B1
(45) Date of Patent: Mar. 19, 2002

(54) ASYMMETRIC HYDROGENATION OF β-KETO ESTERS

(75) Inventors: Rainer Stürmer, Rödersheim-Gronau; Martin Jochen Klatt, Bad Dürkheim; Armin Börmer, Rostock; Jens Holz, Rostock; Gudrun Voss, Rostock, all of (DE)

(73) Assignee: BASF Aktienegesellschaft, Ludwigshafen (DE)

( * ) Notice: Subject to any disclaimer, the term of this patent is extended or adjusted under 35 U.S.C. 154(b) by 0 days.

(21) Appl. No.: 09/407,283

(22) Filed: Sep. 29, 1999

(30) Foreign Application Priority Data

Oct. 2, 1998 (DE) .......................... 198 45 517

(51) Int. Cl.[7] .......................... C07C 69/74; C07F 9/50
(52) U.S. Cl. .................. 560/125; 560/105; 560/126; 560/127; 560/128; 560/145; 560/165; 560/180; 556/16; 556/18; 556/21; 556/23
(58) Field of Search ................. 560/126, 127, 560/128, 145, 180, 165, 265, 125; 556/16, 18, 21, 23

(56) References Cited

U.S. PATENT DOCUMENTS 6,013,833 A * 1/2000 Gewald et al.
6,214,763 B1 * 4/2001 Dobbs et al.
6,225,487 B1 * 5/2001 Guram

FOREIGN PATENT DOCUMENTS

| EP | 863125 | 9/1998 |
|---|---|---|
| WO | 92/19630 | 11/1992 |
| WO | 97/13763 | 4/1997 |

OTHER PUBLICATIONS

Burk et al., *J. Am. Chem. Soc.*, 1995, 117, 4423–4424.
Haack et al., *Angew. Chem. Int. Ed. Engl.*, 1997, 36(3), 285–288.
Roucoux et al., *Tetrahedron Asymmetry*, 7(2), 379–382, 1996.
Puntener et al., *Tetrahedron Letters*, 37(45), 8165–8168, 1996.
Sammakia et al., *J. Org. Chem.*, 1997, 62, 6104–6105.

* cited by examiner

*Primary Examiner*—Gary Geist
*Assistant Examiner*—Robert W. Deemie
(74) *Attorney, Agent, or Firm*—Keil & Weinkauf

(57) ABSTRACT

Enantiomerically pure β-hydroxy esters are prepared by a process in which β-keto esters are reacted with hydrogen in the presence of catalysts of the formula $LRuX_2$ where X is halogen, acetate, allyl, methallyl, 2-phenylallyl, perchlorate, trifluoroacetate, tetrafluoroborate, hexafluoroantimonate, hexafluorophosphate, hexafluoroarsenate or trichloroacetate, L is a bidentate phospholane of the formula I

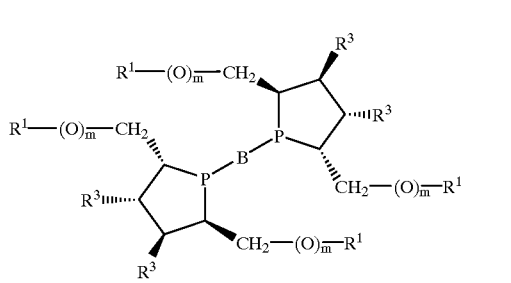

where
B=a bridging link with 1–5 carbon atoms between the two phosphorus atoms,
$R^1$=H, $C_1$–$C_6$-alkyl, aryl, alkylaryl or $SiR^2_3$,
$R^2$=alkyl or aryl,
m=0 or 1,
$R^3$=H or $OR^4$, and
$R^4$=$R^1$,
with the proviso that if m=1 then $R^3$=H and if m=0 then $R^3 \neq $ H.

9 Claims, No Drawings

ASYMMETRIC HYDROGENATION OF β-KETO ESTERS

BACKGROUND OF THE INVENTION

1. Field of the Invention

The present invention relates to a process for preparing enantiomerically pure β-hydroxy esters by hydrogenation in the presence of ruthenium catalysts.

2. Description of the Related Art

The catalytic hydrogenation of ketones and β-keto esters with Ru-diphosphine complexes is known (e.g. Burk et al., J. Am. Chem. Soc. 1995, 117, 4423; A. Mortreux et al., Tetrahedron: Asymmetry, 7(2), 379–82, 1996; Noyori et al., Angew. Chem., Int. Ed. Engl., 36(3), 285–288, 1997; WO 9713763 A1).

The catalytic transfer hydrogenation of ketones with formic acid/triethylamine complex as reducing agent and ruthenium catalysts is also known (P. Knochel et al., Tetrahedron Lett., 37(45), 8165–8168, 1996; Sammakia et al., J. Org. Chem., 62(18), 6104–6105, 1997 (isopropanol as reducing agent)).

A common feature of all these methods is that the ligands and catalysts used are very awkward to prepare. In the transfer hydrogenations, furthermore, it is not the inexpensive hydrogen which is used but isopropanol or formic acid/tertiary amines instead. When the latter is used in the reaction it makes workup more difficult and automatically produces acetone or carbon dioxide.

In addition, the amounts of catalyst employed in these reactions are generally very large; this makes the prior art processes uneconomic.

BRIEF SUMMARY OF THE INVENTION

It is an object of the present invention to discover a process for hydrogenating keto esters which operates with hydrogen as reducing agent, uses a catalyst which is easy to prepare, permits a high substrate:catalyst ratio, and operates with high enantioselectivity.

DETAILED DESCRIPTION OF THE INVENTION

We have found that this object is achieved by a process for preparing enantiomerically pure β-hydroxy esters by reacting β-keto esters with hydrogen in the presence of catalysts of the formula $LRuX_2$ where X is halogen, acetate, allyl, methallyl, 2-phenylallyl, per-chlorate, trifluoroacetate, tetrafluoroborate, hexafluoroan-timonate, hexafluorophosphate, hexafluoroarsenate, trichlo-roacetate, L is a bidentate phospholane of the formula I

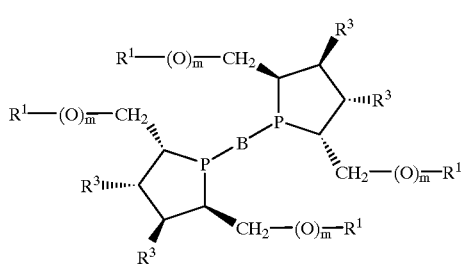

where

B=is a bridging link with 1–5 carbon atoms between the two phosphorus atoms, $R^1$=H, $C_1$–$C_6$-alkyl, aryl, alkylaryl or $SiR^2_3$,
$R^2$=alkyl or aryl,
m=0 or 1,
$R^3$=H or $OR^4$, and
$R^4$=$R^1$, with the proviso that if m=1 then $R^3$=H and if m=0 then $R^3 \neq H$.

Preferred bridging links B are those where

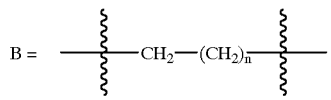

where n = 0, 1, 2, 3 or 4 or

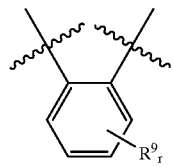

where r = 0, 1, 2 or 3,
$R^9$ = alkyl or
fused-on aryl

Particular preference is given to bridging links B where n=1 or 2 or r=0.

The preparation of the bidentate phospholane ligands L is described in patent applications DE 19725796.8 and DE 19824121.6 and in the experimental section of this specification.

The preparation starts from the sugar mannitol, which is available in enantiomerically pure form from natural sources.

The catalytically active ruthenium complexes $LRuX_2$ can be prepared by conventional reaction (e.g. Uson, Inorg. Chim. Acta 73, 275 (1983), EP-A 0158875, EP-A 437690) with ruthenium complexes containing labile ligands (e.g. $[RuCl_2(COD)]_n$, p-cymene-ruthenium chloride dimer).

The hydrogenation of the invention is generally conducted at a temperature from −20 to 150° C., preferably from 0 to 100° C. and, with particular preference, from 15 to 40° C.

For the hydrogenation process of the invention the hydrogen pressure can be varied within a wide range between 0.1 and 300 bar. Very good results are obtained within a pressure range from 1 to 100 bar, preferably from 1 to 50 bar.

The reaction is preferably conducted in a solvent which comprises an alkanol.

Preferred solvents for the hydrogenations are $C_1$–$C_4$-alkanols, especially MeOH. In the case of poorly soluble substrates suitability extends to solvent mixtures, such as methanol and $CH_2Cl_2$, THF, toluene, or else water.

It is particularly preferred to use the alkanol on which the β-keto ester substrate is based, since this prevents unwanted transesterifications.

The catalyst is commonly employed in amounts of from 1:10 to 1:1,000,000, preferably from 1:1000 to 1:100,000 (w/w), based on the hydrogenation substrate.

The reaction can be improved in terms of both yield and selectivity by adding an acid, especially a strong acid, such as mineral acids or trifluoro- or trichloroacetic acids.

In this case the acid is generally added in an amount of 0.5–2 mol equivalents, based on catalyst.

EXPERIMENTAL SECTION
EXAMPLE 1
Preparing a diphospholane L
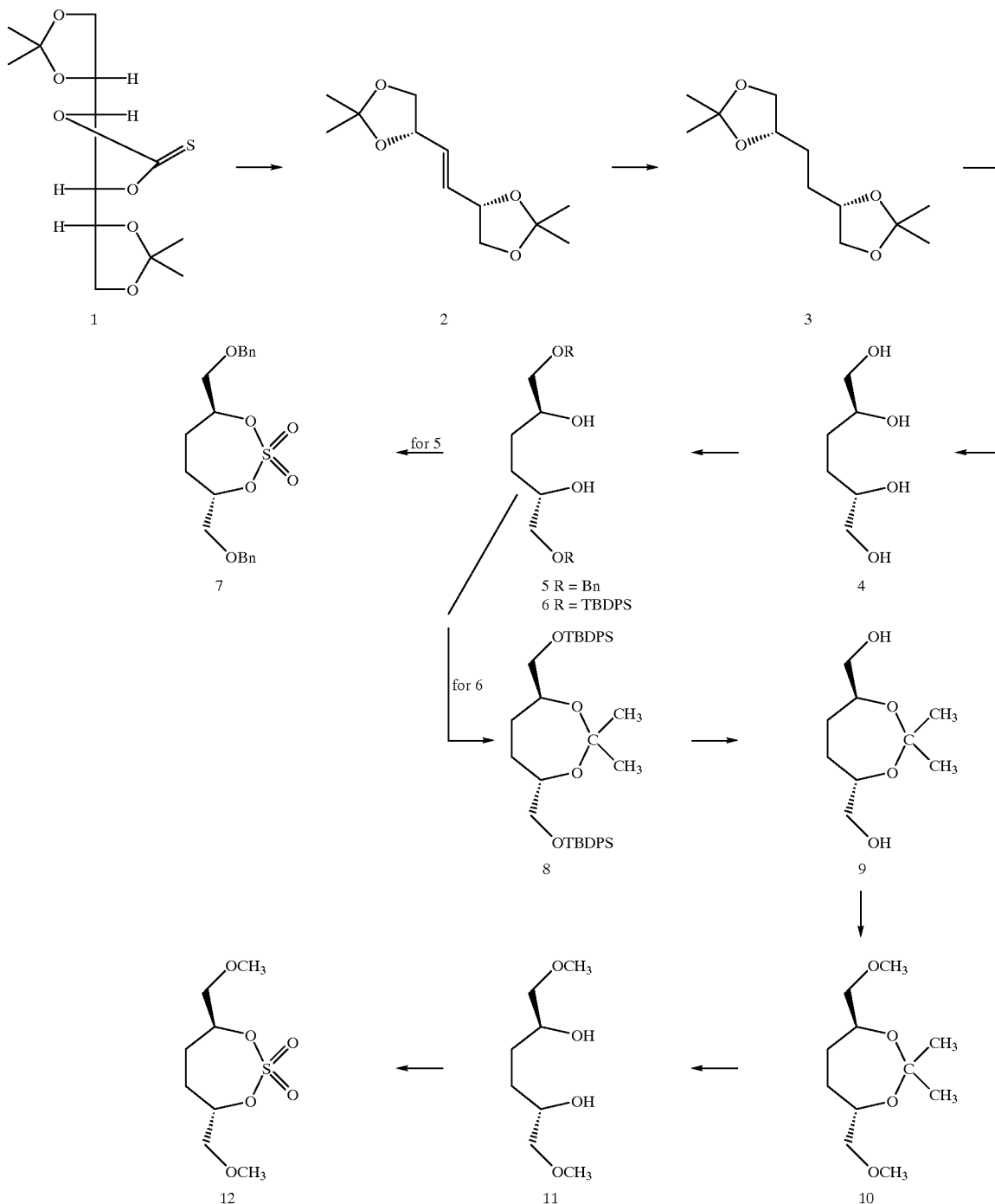

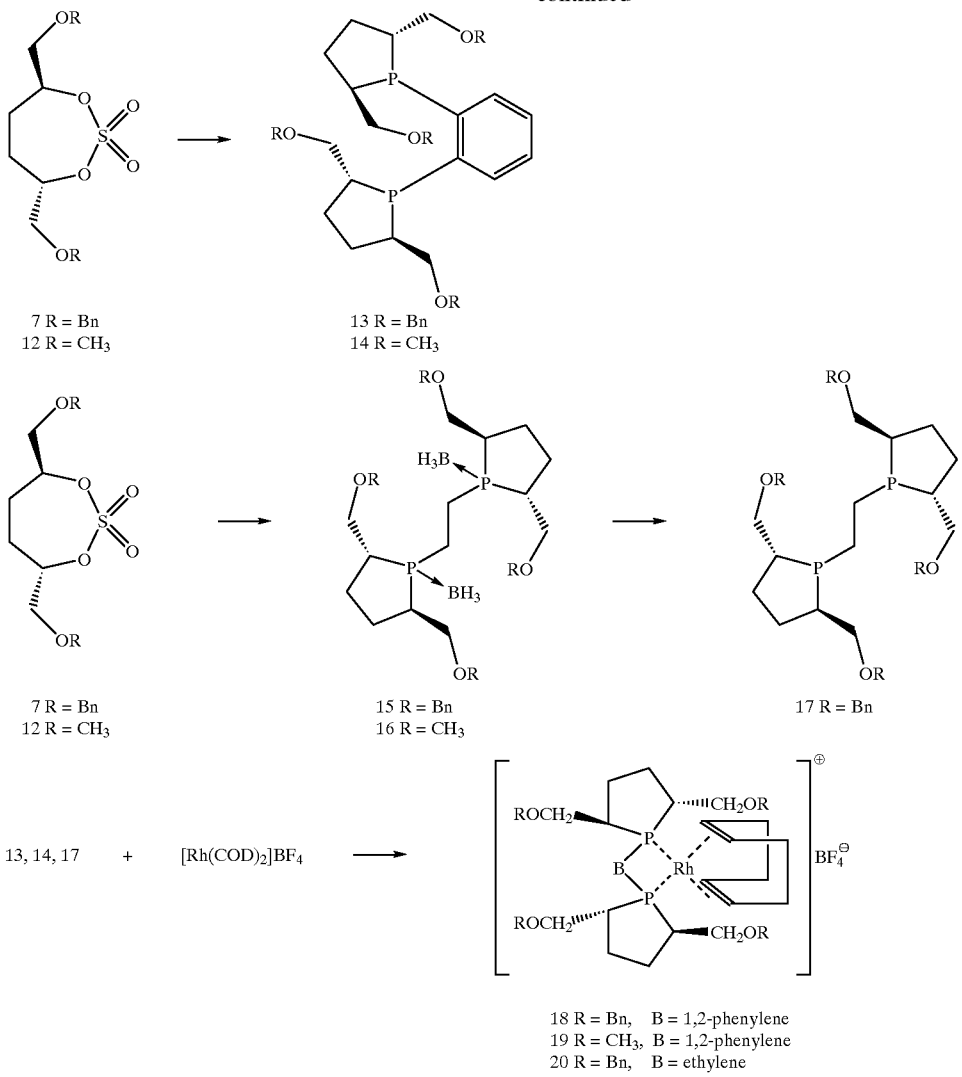

7 R = Bn
12 R = CH₃

13 R = Bn
14 R = CH₃

7 R = Bn
12 R = CH₃

15 R = Bn
16 R = CH₃

17 R = Bn

18 R = Bn, B = 1,2-phenylene
19 R = CH₃, B = 1,2-phenylene
20 R = Bn, B = ethylene 1,2;5,6-Di-O-isopropylidene-3,4-O-thiocarbonyl-D-mannitol (1):

Using the method of E.J. Corey et al.[1] 1,2;5,6-di-O-isopropylidene-D-mannitol was reacted with thiophosgene in the presence of 4-dimethylaminopyridine in methylene chloride, with a yield of 90%.

E-3,4-Didehydro-3,4-dideoxy-1,2;5,6-di-O-isopropylidene-D-threo-hexitol (2):

The cyclic thiocarbonate 1 was heated in triethyl phosphite for 20 hours in accordance with the literature[2,3] to give the trans-olefin in yields of 80 to 90%.

3,4-Dideoxy-1,2;5,6-di-O-isopropylidene-D-threo-hexitol (3):

In a modification of the method of Machinaga et al.[4] the olefin 2 (10 g) was hydrogenated in methanol with 10% platinum on active carbon (250 mg) at atmospheric pressure to give the compound 3. After purification by column chromatography the yield was 80 to 90%. Compound 3 can also be purified by distillation in accordance with the literature[4] (b.p. 0.6 mm=73° C.).

3,4-Dideoxy-D-threo-hexitol (4):

The acidic hydrolysis of the isopropylidene groups was carried out in accordance with the literature[4] in 1 N hydrochloric acid. Recrystallization gave the compound in the yield of 85%.

(2S,5S)-1,6-Bis(benzyloxy)hexane-2,5-diol (5):

Following the procedure of Marzi et al.[5] 3.0 g (20 mmol) of the 3,4-dideoxy-D-threo-hexitol (4) were converted into 3.70 g of the 1,6-di-O-benzylated product 5 in a yield of 56%.

(2S, 5S) -1,6-Bis[(tert-butyldiphenylsilyl)oxy]hexane-2,5-diol (6):

In accordance with the literature[5] 3.0 g (20 mmol) of the compound 4 in DMF were reacted with tert-butyldiphenylchlorosilane in the presence of imidazole to give the derivative 6 in a yield of 80%.

(4S,7S)-4,7-Bis(benzyloxymethyl)-2,2-dioxo[1,3,2] dioxothiepan (7):

3.30 g (10 mmol) of the diol 5 in 70 ml of dry carbon tetrachloride were slowly admixed under argon with 1.43 g (12 mmol) of thionyl chloride and the resulting mixture was then heated at reflux for 90 minutes. After the solvent had been removed on a rotary evaporator the residue was taken up in a mixture of carbon tetrachloride (40 ml), acetonitrile (40 ml) and water (60 ml), and 15 mg (72 μmol) of RuCl₃*3H₂O and 4.28 g (20 mmol) of sodium periodate were added at 0° C. The mixture was then stirred at room temperature for one hour, after which 50 ml of water were added to the suspension. Subsequent extraction with diethyl ether (3×75 ml) and washing of the organic phase with saturated NaCl solution (100 ml) gave, after drying (Na$_2$SO$_4$), a residue which by column chromatography (n-hexane:AcOEt=2:1, R$_f$=0.20) gave the compound 7 in a yield of 3.37 g (86%).

m.p.=57 to 59° C.; $[\alpha]_D^{26}$=−37.2° (c 1.01; CHCl$_3$); $^1$H-NMR (CDCl$_3$, 400 MHz) δ 7.34 (10H, m, arom. H), 4.78 (2H, m, H-2/5), 4.57 (2H, AB sp., H$_a$—CH$_2$Ph, $^2$J$_{a,b}$=12.0 Hz), 4.56 (2H, AB sp., H$_b$—CH$_2$Ph, $^2$J$_{a,b}$=12.0 Hz), 3.65 (2H, dd, H$_a$—CH$_2$OH, $^2$J$_{a,b}$=10.8 Hz, $^3$J$_{H,H}$=5.4 Hz), 3.56 (2H, dd, H$_b$—CH$_2$OH, $^2$J$_{a,b}$=10.8 Hz, $^3$J$_{H,H}$=4.9 Hz), 2.00 (4H, m, H-3/4); $^{13}$C-NMR (CDCl$_3$, 100 MHz) δ 137.3, 128.4–127.7 (arom. C), 82.6 (C-2/5), 73.4 (CH$_2$Ph), 70.8 (C-1/6), 28.9 (C-3/4); Elemental analysis C$_{20}$H$_{24}$O$_6$S (392.47) calc.: C 61.21, H 6.16, S 8.17; found: C 61.03, H 6.19, S 8.10.

1,6-Di-O-(tert-butyldiphenyl)silyl-2,5-di-O-isopropylidene-3,4-dideoxy-D-threo-hexitol (8):

In accordance with the literature[5] 6.27 g (10 mmol) of the compound 6 were reacted to give the isopropylidene derivative 8 in a yield of 85% (5.67 g). 8 was purified by column chromatography (n-hexane:diethyl ether=19:1, R$_f$=0.2) for the purpose of characterization. For the subsequent reaction step it was possible to dispense with purifying the compound.

2,5-Di-O-isopropylidene-3,4-dideoxy-D-threo-hexitol (9):

The silyl groups of 6.67 g (10 mmol) of the silyl compound 8 were eliminated with tetrabutylammonium fluoride in THF[5] and subsequent chromatographic purification (diethyl ether:MeOH=19:1, R$_f$=0.5) gave 1.7 g (89%) of the diol 9.

2,5-Di-O-isopropylidene-1,6-di-O-methyl-3,4-dideoxy-D-threo-hexitol (10):

A solution of 3.80 g (20 mmol) of the diol 9 in 30 ml of THF was added at 0° C. to a solution of 1.06 g (44 mmol) of NaH in 60 ml of THF. After the alkoxide had finished forming 2.2 equivalents of methyl iodide were slowly added (6.21 g, 44 mmol) and the mixture was stirred at room temperature. After the end of the reaction the excess NaH was carefully destroyed with water (30 ml) and the THF was removed under reduced pressure. The aqueous solution remaining was then extracted with methylene chloride (3×50 ml) and the combined organic phases were dried (Na$_2$SO$_4$) and concentrated. Column chromatography of the resulting residue (n-hexane:AcOEt=2:1, R$_f$=0.40) gave a colorless sirup in a yield of 84% (3.68 g).

Syrup; $[\alpha]_D^{23}$=−32.8° (c 1,01, CHCl$_3$); $^1$H-NMR (CDCl$_3$, 400 MHz) δ 3.92 (2H, m, H-2/5), 3.32 (2H, dd, H$_a$—CH$_2$O, $^2$J$_{a,b}$=9.9 Hz, $^3$J$_{H,H}$=6.3 Hz), 3.30 (6H, s, CH$_3$), 3.55 (2H, m, H$_b$—CH$_2$O, $^2$J$_{a,b}$=9.9 Hz, $^3$J$_{H,H}$=5.3 Hz), 1.67 (2H, m, H$_a$-3/4), 1.34 (2H, m, H$_b$-3/4), 1.31 (6H, s, CH$_3$); $^{13}$C-NMR (CDCl$_3$, 100 MHz) δ 100.5 (C(O)$_2$), 76.2 (C-1/6), 70.4 (C-2/5), 59.1 (CH$_3$), 31.1 (C-3/4), 25.6 (C(CH$_3$)$_2$); Elemental analysis C$_{11}$H$_{22}$O$_4$ (218.293) calc.: C 60.52, H 10.16; found: C 60.38, H 10.07.

(2S,5S)-1,6-Bis(benzyloxy)hexane-2,5-diol (11): 4.0 g (18.32 mmol) of the compound 10 were hydrolyzed in a mixture of 60 ml of THF and 60 ml of 1 N hydrochloric acid over a period of 20 minutes. Following the concentration of the solution on a rotary evaporator 3.20 g of a pale yellow sirup 11 were obtained by chromatography (EtOH:AcOEt=1:3, R$_f$=0.45) in virtually quantitative yield.

Syrup; $[\alpha]_D^{22}$=−7.2° (c 1.09, CH$_3$OH); $^1$H-NMR (CD$_3$OD, 400 MHz) δ 3.72 (2H, m, H-2/5), 3.37 (6H, s, CH$_3$), 3.38–3.30 (4H, m, CH$_2$OH), 1.56 (4H, m, H-3/4); $^{13}$C-NMR (CD$_3$OD, 100 MHz) δ 78.2 (C-1/6), 70.1 (C-2/5), 59.2 (CH$_3$), 30.6 (C-3/4); Elemental analysis C$_8$H$_{18}$O$_4$ (178.228) calc.: C 53.91, H 10.18; found: C 53.47, H 10.14.

(4S,7S)-4,7-Bis(methyloxymethyl)-2,2-dioxo[1,3,2] dioxothiepan (12):

In analogy to the preparation of the cyclic sulfate 7, 1.78 g (10 mmol) of the diol 11 were converted into the target compound 12. Chromatographic purification (n-hexane:AcOEt=1:2, R$_f$=0.4) was unnecessary here since the product 12 could be isolated by recrystallization from diethyl ether/n-hexane as a white solid in a yield of 76% (1.83 g).

m.p.=75–78° C.; $[\alpha]_D^{23}$=−44.15 (c 1.01; CHCl$_3$); $^1$H-NMR (CDCl$_3$, 400 MHz) δ 4.72 (2H, m, H-2/5), 3.56 (2H, dd, H$_a$—CH$_2$O, $^2$J$_{a,b}$=10.8 Hz, $^3$J$_{H,H}$=5.4 Hz), 3.47 (2H, dd, H$_a$—CH$_2$O, $^2$J$_{a,b}$=10.8 Hz, $^3$J$_{H,H}$=4.7 Hz), 3.37 (6H, s, CH$_3$), 2.04–1.92 (4H, m, H-3/4); $^{13}$C-NMR (CDCl$_3$, 100 MHz) δ 82.5 (C-2/5), 73.4 (C-1/6), 59.3 (OCH$_3$), 28.8 (C-3/4); Elemental analysis C$_8$H$_{16}$O$_6$S (240.274) calc.: C 39.99, H 6.71, S 13,34; found: C 40.06, H 6.76, S 1.27.

1,2-Bis[(2R,5R)-2,5-benzyloxymethylpholanyl] benzene (13):

0.52 g (3.66 mmol) of 1,2-bis(phosphanyl)benzene in 50 ml of THF was slowly admixed with 2.0 equivalents of n-BuLi (4.58 ml, 1.6 M solution in n-hexane) and after two hours the resultant yellow solution was admixed slowly with 2.86 g (7.32 mmol) of the cyclic sulfate 7 in 20 ml of THF. The mixture was stirred at room temperature for 2 hours more and then finally a further 2.2 equivalents of n-BuLi (5.03 ml, 1.6 M solution in n-hexane) were added. The solution was stirred overnight and the excess BuLi was finally destroyed with 2 ml of MeOH. The solvent was removed under reduced pressure and the residue was taken up in 20 ml of water under anaerobic conditions and then extracted with methylene chloride (2×50 ml). The organic phase was dried (Na$_2$SO$_4$), the solvent was removed and the desired product was isolated by column chromatography (n-hexane:AcOEt=4:1, R$_f$=0.35) as a pale yellow sirup in a yield of 0.52 g (19%).

Syrup; $^1$H-NMR (CDCl$_3$, 400 MHz) δ 7.45–7.10 (24H, m, arom. H), 4.49 (2H, AB sp., H$_a$—CH$_2$Ph, $^2$J$_{a,b}$=12.1 Hz), 4.47 (2H, AB sp., H$_b$—CH$_2$Ph, $^2$J$_{a,b}$=12.1 Hz), 4.18 (2H, AB sp., H$_a$—CH$_2$Ph, $^2$J$_{a,b}$=11.9 Hz), 4.04 (2H, AB sp., H$_b$—CH$_2$Ph, $^2$J$_{a,b}$=11.9 Hz), 3.65–3.45 (4H, m, CH$_2$O), 2.97–2.80 (4H, m, CH$_2$O), 2.70 (2H, m, CH—P); 2.33 (4H, m, CH—P, H$_a$—(CH$_2$)$_2$); 2.18 (2H, m, H$_a$—(CH$_2$)$_2$), 1.80–1.53 (4H, m, H$_b$—(CH$_2$)$_2$); $^{13}$C-NMR (CDCl$_3$, 100 MHz) δ 141.8 (m, C$_{ar}$—P), 138.6+138.5 (ipso-C), 131.8, 128.4–127.1 (arom. C), 74.1 (m, CH$_2$Ph), 73.0 (CH$_2$Ph), 72.5 (CH$_2$O), 72.5 (CH$_2$O), 39.5 (CH—P), 38.9 (m, CH—P), 30.9 (CH$_2$), 30.4 (CH$_2$); $^{31}$P-NMR (CDCl$_3$, 162 MHz) δ 11.5;

1,2-Bis[(2R,5R)-2,5-benzyloxymethylphospholanyl] benzene (14):

In analogy to the preparation of bisphospholane 13, the compound 12 instead of the cyclic sulfate 7 was reacted to give the desired methoxymethyl-substituted bisphospholane 14. After purification by column chromatography (n-hexane: AcOEt=2:1, R$_f$=0.20) the colorless sirup was isolated in a yield of 0.80 g (48%).

Syrup; $^1$H-NMR (CDCl$_3$, 400 MHz) δ 7.45 (2H, m, arom. H), 7.30 (2H, m, arom. H), 3.55 (4H, m, CH$_2$O), 3.36 (2H, m, CH$_2$O), 3.35 (6H, s, CH$_3$), 3.10 (6H, s, CH$_3$), 2.90 (2H, m, CH$_2$O), 2.78 (2H, m, CH—P), 2.63 (2H, m, CH—P), 2.32 (2H, m, CH$_2$); 2.16 (4H, m, CH$_2$); 1.68 (2H, m, CH$_2$), 1.55 (4H, m, CH$_2$); $^{13}$C-NMR (CDCl$_3$, 100 MHz) δ 141.9 (m, C$_{ar}$—P), 131.8, 128.4 (arom. C), 74.1 (m, CH$_2$Ph), 76.6 (m, CH$_2$O), 74.5 (CH$_2$O), 58.8 (CH$_3$), 58.2 (CH$_3$), 39.6 (CH—P), 39.0 (m, CH—P), 30.9 (CH$_2$), 30.3 (CH$_2$); $^{31}$P-NMR (CDCl$_3$, 162 MHz) δ−11.7.

1,2-is[(2R,5R)-2,5-benzyloxymethylphospholanyl]ethaneborane complex (15):

348 mg (3.70 mmol) of bis(phosphanyl)ethane were admixed at room temperature in THF with 7.40 mmol (4.63 ml) of a 1.6 M n-BuLi solution in hexane and the mixture was stirred for two hours. Then a solution of 2.90 g (7.40 mmol) of the cyclic sulfate 7 in 20 ml of THF was added slowly and stirring was continued for two hours more. The reaction was completed by subsequent addition of a further 5.09 ml (8.14 mmol) of n-BuLi solution and the reaction mixture was stirred overnight. To form the borane adduct the solution was cooled to −20° C. and 9.25 ml (9.25 mmol) of 1 M BH$_3$*THF solution were added. After two hours, excess BuLi and BH$_3$ were destroyed by adding 2 ml of MeOH and the solvent was removed under reduced pressure. The residue was taken up in water and then extracted with methylene chloride. The extracts were subsequently dried (Na$_2$SO$_4$) and concentrated and the residue which remained was purified by column chromatography (n-hexane: AcOEt=4:1, R$_f$=0.20). This gave 350 mg (13%) of a viscous sirup.

Syrup; $^1$H-NMR (CDCl$_3$, 400 MHz) δ 7.37–7.22 (20H, m, arom. H), 4.47 (2H, AB sp., H$_a$—CH$_2$Ph, $^2$J$_{a,b}$=11.2 Hz), 4.42 (2H, AB sp., H$_a$—CH$_2$Ph, $^2$J$_{a,b}$=12.1 Hz), 4.41 (2H, AB sp., H$_b$—CH$_2$Ph, $^2$J$_{a,b}$=12.1 Hz), 4.38 (2H, AB sp., H$_b$—CH$_2$Ph, $^2$J$_{a,b}$=11.2 Hz), 3.58 (4H, m, CH$_2$O), 3.43 (4H, m, CH$_2$O), 2.37 (2H, m, CH—P); 2.14–1.79 (10H, m, CH—P, (CH$_2$)$_2$), 1.41–1.20 (2H, m, (CH$_2$)$_2$), 0.85–0.00 (6H, m, BH$_3$); $^{13}$C-NMR (CDCl$_3$, 100 MHz) δ 138.1+137.9 (ipso-C), 128.3–127.4 (arom. C), 73.2 (CH$_2$Ph), 72.7 (CH$_2$Ph), 69.4 (CH$_2$O), 68.4 (CH$_2$O), 39.5 (m, CH—P), 29.1 (CH$_2$), 28.6 (CH$_2$), 15.9 (m, CH$_2$)$_2$); $^{31}$P-NMR (CDCl$_3$, 162 MHz) δ 40.2.

1,2-Bis[(2R,5R)-2,5-methyloxymethylphospholanyl] ethane-borane complex (16):

In analogy to the preparation of compound 15, 2.14 g (8.91 mmol) of cyclic sulfate 12 and 0.42 g (4.45 mmol) of bis(phosphanyl)ethane were reacted to give the desired borane-protected bisphospholane 16. It was purified by chromatography with n-hexane:AcOEt=2:1 (R$_f$=0.15). This gave a crystalline product in a yield of 0.71 g (39%).

m.p.=45–48° C.; [α]$_D^{23}$=21.9° (c 1.00; CHCl$_3$); $^1$H-NMR (CDCl$_3$, 400 MHz) δ 3.51 (8H, m, CH$_2$O), 3.33 (6H, s, CH$_3$O), 3.32 (6H, m, CH$_3$O), 2.36 (2H, m, CH—P); 2.23–2.05 (6H, m, CH—P, (CH$_2$)$_2$), 1.96 (4H, m, CH$_2$)$_2$), 1.58–1.35 (4H, m, (CH$_2$)$_2$), 0.95–0.00 (6H, m, BH$_3$); $^{13}$C-NMR (CDCl$_3$, 100 MHz) δ 71.6 (m, CH$_2$O), 70.8 (CH$_2$O), 58.7 (CH$_3$O), 58.7 (CH$_3$O), 39.5 (m, CH—P), 29.1 (CH$_2$), 28.9 (CH$_2$), 15.8 (m, CH$_2$)$_2$); $^{31}$P-NMR (CDCl$_3$, 162 MHz): δ 40.5; MS (m/z; EI) 391 [M$^+$—BH$_4$] (100).

1,2-Bis[(2R,5R)-2,5-benzyloxymethylphospholanyl]ethane (17): 0.30 g (0.42 mmol) of the borane complex 15 was admixed with an anaerobic solution of 0.142 g (1.26 mmol) of DABCO in 6 ml of toluene and the mixture was stirred at 40° C. Following complete reaction the solution was concentrated and quickly purified by column chromatography (n-hexane:AcOEt=4:1, R$_f$=0.55). The bisphospholane 17 was obtained in a yield of 0.21 g (73%) and was employed immediately for complexation.

Syrup; $^1$H-NMR (CDCl$_3$, 400 MHz) δ 7.35–7.21 (20H, m, arom. H), 4.52 (2H, AB sp., H$_a$—CH$_2$Ph, $^2$J$_{a,b}$=12.1 Hz), 4.48 (2H, AB sp., H$_b$—CH$_2$Ph, $^2$J$_{a,b}$=12.1 Hz), 4.43 (2H, AB sp., H$_a$—CH$_2$Ph, $^2$J$_{a,b}$=12.1 Hz), 4.41 (2H, AB sp., H$_b$—CH$_2$Ph, $^2$J$_{a,b}$=12.1 Hz), 3.61–3.41 (8H, m, CH$_2$O), 2.29 (2H, m, CH—P); 2.20 (2H, m, CH—P); 2.07 (4H, m, H$_a$—(CH$_2$)$_2$), 1.53–1.23 (8H, m, H$_b$—(CH$_2$)$_2$), (CH$_2$)$_2$); $^{13}$C-NMR (CDCl$_3$, 100 MHz) δ 138.6+138.4 (ipso-C), 128.3–127.3 (arom. C), 74.2 (m, CH$_2$Ph), 72.9 (CH$_2$Ph), 72.7 (CH$_2$O), 70.2 (CH$_2$O), 43.7 (m, CH—P), 40.0 (m, CH—P), 31.4 (CH$_2$), 31.3 (CH$_2$), 19.1 (m, CH$_2$)$_2$); $^{31}$P-NMR (CDCl$_3$, 162 MHz): δ −6.9.

EXAMPLE 2

Preparing a diphospholane L 1,2;5,6-Di-O-isopropylidene-D-mannitol (1): obtainable commercially from FLUKA (Order No. 38410).

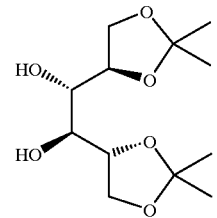

3,4-Di-O-benzyl-1,2;5,6-di-O-isopropylidene-D-mannitol (2): prepared according to: J. Jurcak, T. Bauer, M. Chmielewski, *Carbohydr. Res.* 164 (1987) 493.

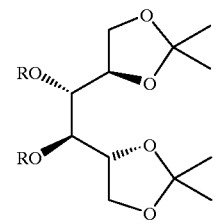

3,4-Di-O-benzyl-D-mannitol (3): prepared according to: J. Jurcak, T. Bauer, M. Chmielewski, *Carbohydr. Res.* 164 (1987) 493.

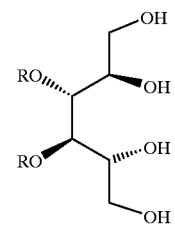

3,4-Di-O-benzyl-1,6-di-O-toluenesulfonyl-D-mannitol (4): prepared according to: J. Fittremann, A. Dureault, J.-C. Depezay, *Tetrahedron Letters* 35 (1994) 1201.

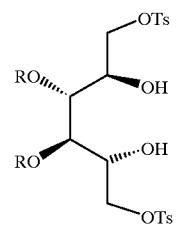

(2R,3R,4R,5R)-3,4-Dibenzyloxyhexane-2,5-diol (5):

A solution consisting of 10 g (14.9 mmol) of the ditosylate 4 in 30 ml of THF is added slowly dropwise at room temperature to a suspension of 2.25 g (59.6 mmol) of LiAlH$_4$ in 100 ml of THF. The suspension is stirred for one hour and then refluxed for two hours. On cooling, the hydride is destroyed by careful successive addition of 2.25 ml of water, 2.25 ml of 15% strength NaOH and a further 6.75 ml of water. The solution is filtered to remove the precipitated inorganic compounds and the residue is extracted with methylene chloride in a Soxhlet apparatus. The combined solutions are dried and, after the solvents have been removed by distillation, the residue is purified by column chromatography (n-hexane:AcOEt 1:2; R$_f$=0.45).

Yield: 3.6 g (73%), white solid, m.p.=46–50° C. [α]$_D^{26}$=−4.7 (c 0.990, CHCl$_3$), $^1$H-NMR (CDCl$_3$): 7.40–7.25 (10 H, m, arom. H), 4.65 (4H, AB sp., CH$_2$Ph, $^2$J$_{A,B}$=11.3 Hz), 4.09 (2H, m, H-2+H-5), 3.53 (2H, m, H-3+H-4), 2.96 (2H, s (Br), 2×OH), 1.25 (6H, d, 2×CH$_3$, $^3$J$_{H,H}$=6.4Hz); $^{13}$C-NMR (CDCl$_3$): 137.4, 128.5, 128.2, 128.0 (arom. C), 81.5 (C-3+C-4), 73.3 (2×CH$_2$Ph), 67.3 (C-2+C-5), 19.7 (2×CH$_3$; IR (KBr): 3417, 3287, 3031, 2987, 2965, 2934, 2882, 1455, 1316, 1210, 1112, 1092, 1075, 1056, 1028, 764, 726, 697; MS (70 eV, m/z): 331 [M$^+$+H] (1), 297 [M$^+$—CH$_3$—H$_2$O] (1), 285 [M—C$_2$H$_5$O] (2); C$_{20}$H$_{26}$O$_4$ (330.43) calc.: C: 72.70% H: 7.93%; found: C: 72.79% H: 7.94%.

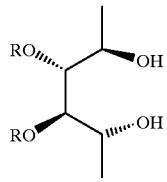

(4R, 5R, 6R, 7R)-5,6-Dibenzyloxy-4,7-dimethyl[1,3,2] dioxathiepan 2,2-dioxide (6):

4.75 g (14.4 mmol) of the diol 5 in 20 ml of carbon tetrachloride are heated under reflux with 1.3 ml of thionyl chloride for 1.5 h. After the mixture has cooled the solvent is removed on a rotary evaporator and the residue obtained is taken up in 10 ml of carbon tetrachloride, 10 ml of acetonitrile and 15 ml of water. The solution is cooled to 0° C. and then 0.021 g (0.08 mmol) of RuCl$_3$*3H$_2$O is added followed by 6.2 g (29.0 mmol) of sodium periodate. The solution is stirred for one hour at room temperature, admixed with 75 ml of water and extracted with 4×100 ml of diethyl ether. The combined extracts are washed once with saturated NaCl solution then dried over Na$_2$SO$_4$ and filtered through kieselguhr. The ethereal solution is concentrated and the cyclic sulfate 6 is purified by column chromatography (n-hexane:AcOEt=9:1, R$_f$=0.25).

Yield 3.4 g (60%) of white crystals. m.p.=90–94° C. [α]$^{23}$$_D$=-2.8 (c 1.012, CHCl$_3$). $^1$H-NMR (CDCl$_3$): 7.40–7.25 (10 H, m, arom. H), 4.79 (4H, AB sp., CH$_2$Ph, $^2$J$_{A,B}$=10.8 Hz), 4.09 (2H, m, H-2+H-5), 3.55 (2H, m, H-3+H-4), 1.53 (6H, d, 2×CH$_3$, $^3$J$_{H,H}$=6.4Hz); $^{13}$C-NMR (CDCl$_3$): 137.1, 128.6, 128.1, 127.7 (arom. C), 84.2 (C-3+C-4), 79.4 (C-2+C-5), 76.2 (2×CH$_2$Ph), 17.9 (2×CH$_3$); IR (KBr): 3090, 3062, 3027, 2989, 2939, 2881, 2861, 1498, 1453, 1395, 1380, 1349, 1208, 1103, 1071, 1020, 949, 899, 841, 750, 741, 703, 699, 611; MS (70 eV, m/z): 392 [M$^+$] (1), 301 [M$^+$—C$_7$H$_7$] (47), 195 [M$^{+-C}$$_7$H$_7$—C$_7$H$_6$O] (36), 91 [C$^7$H$_7^{+1}$ (100); C$_{20}$H$_{24}$O$_6$S (392.47) calc.: C: 61.21% H: 6.16% S: 8.17%; found: C: 61.20% H: 6.24% S: 8.08%.

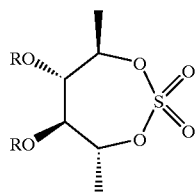

1,2-Bis(( 4S,5S, 6S,7S)-5,6-dibenzyloxy-4,7-dimethylphospholanyl)-benzene (7):

A solution of 0.564 g (3.96 mmol) of 1,2-bis(phosphanyl) benzene in 70 ml of THF is admixed dropwise with 4.95 ml (7.93 mmol) of n-BuLi (1.6 M in hexane) at room temperature. The clear yellow solution which forms is stirred for 2 hours more and then slowly admixed with a solution of 3.11 g (7.92 mmol) of cyclic sulfate 6 in 15 ml of THF. The color changes to reddish orange. After four hours a further 5.45 ml (8.71 mmol) of n-BuLi are transferred to the reaction mixture and stirring is continued at room temperature for 16 h. The resultant red solution is worked up by adding 3 ml of methanol and removing the THF under reduced pressure. The residue is taken up in 50 ml of methylene chloride and washed under anaerobic conditions with water (20 ml). Drying (Na$_2$SO$_4$), removal of the solvent and purification by chromatography (n-hexane:AcOEt=9:1, R$_f$=0.2) gives a colorless sirup in a yield of 42%.

$^1$H-NMR (C$_6$D$_6$): 7.70–7.00 (10 H, m, arom. H), 4.50 (8H, m, 4×CH$_2$Ph), 4.05–3.93 (4H, m, H-2+H-5), 3.15–2.94 (4H, m, H-2+H-5), 1.47 (6H, m, CH$_3$), 0.88 (6H, m, CH$_3$); $^{13}$C-NMR (C$_6$D$_6$): 143.3 (m), 139.3, 139.3, 128.5–127.5 (arom. C), 85.2+84.2 (C-3+C-4), 72.2+72.0 (4×CH$_2$Ph), 32.4 (m, C-2+C-5), 14.5 (CH$_3$), 13.4 (CH$_3$); $^{31}$P-NMR (C$_6$D$_6$): -3.4; MS (FD$_{pos}$): 731 [M$^+$+H] (100).

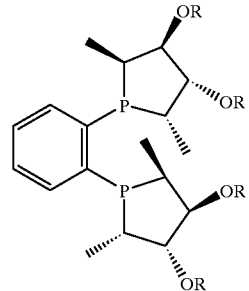

EXAMPLE 3

Preparing the catalyst

Cyclooctadienerutheniumbis(2-methallyl) (100 mg, 0.32 mmol) and 0.32 mmol of the phospholane ligand are introduced into a vessel in 5 ml of heptane and stirred at 60–70° C. for 12 h. The solvent is stripped off and the residue is taken up in 5 ml of methyl ethyl ketone or acetone, to which 2 equivalents of methanolic HBr are added. The mixture is stirred at RT for 2 h, filtered and concentrated. The product is the phospholanoruthenium-dibromine complex.

Instead of HBr it is also possible to use other acids such as HCl, HI, TFA, HBF$_4$ and the like. In that case, complexes with the corresponding counterions are obtained.

EXAMPLE 4

Hydrogenating

The catalyst from Example 3 is dissolved in methanol, and 10,000 equivalents of β-keto ester are added. If desired it is also possible to add water and an acid (0.5–2 eq. (based on catalyst) of an inorganic mineral acid or strong organic acid, such as TFA, trichloroacetic acid and the like). Hydrogen (10 bar) is injected and the reaction mixture is stirred at 35° C. until no more hydrogen is taken up.

EXAMPLES

The following experiments were carried out by the above procedure.

| Ligand | Substrate | S:C | MeOH/H$_2$O | Temp. | Pressure H$_2$ | Time | Conversion | % ee |
|---|---|---|---|---|---|---|---|---|
| Bn-Ro-PHOS | 3-Oxo-1,8-octanoic acid dimethyl ester | 10000:1 | 10:1 | 35 | 10 | 72 | 100 | 96.6 (S) |
| Bn-Ro-PHOS | 3-Oxo-1,8-octanoic acid dimethyl ester | 30000:1 | 15:1 | 35 | 30 | 24 | 97 | 95.8 (S) |
| Bn-Ro-PHOS | 3-Oxo-1,8-octanoic dimethyl ester | 30000:1 | 15:1 + 1.0 eq. TFA | 35 | 30 | 24 | 100 | 98.8 (S) |
| Bn-Ro-PHOS | Acetoacetic acid methyl ester | 15000:1 | 15:1 | 25 | 10 | 16 | 100 | 94.3 (S) |
| Bn-Ro-PHOS | 3-Oxovaleric acid methyl ester | 30000:1 | 15:1 | 35 | 30 | 16 | 100 | 97.0 (S) |
| Bn-Ro-PHOS | Acetoacetic acid ethyl ester | 30000:1 | 15:1 | 25 | 30 | 16 | 100 | 94.5 (S) |

S:C = substrate/catalyst ratio (w/w)

The conversions and enantiomeric excesses were determined by HPLC and GC, respectively.

Analytical data of the (3S)-3-hydroxyoctanedioic acid dimethyl ester

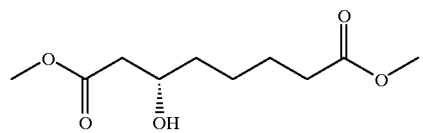

$^1$H-NMR(400 MHz, CDCl$_3$):      $^{13}$C-NMR(100 MHz, CDCl$_3$):

δ:  1.50(m, 4H, 5.6-CH$_2$)          δ:  24.8(5.6-C)
    1.67(μ, 2H, 4-XH$_2$)                25.1(5,6-X)
    2.35(t, J=8Hz, 7-CH$_2$)             33.9(7-C)
    2.47(m, 2H, 2-CH$_2$)                36.2(4-C)
    3.32(s, 1H, OH)                      41.4(2-C)
    3.65(s, 3H, OCH$_3$)                 51.5(OCH$_3$)
    3.70(s, 3H, OCH$_3$)                 51.7(OCH$_3$)
    4.01(m, 1H, CH)                      67.7(3-C)
                                         173.2(ester-C)
                                         174.1(ester-C)

b.p.: 165° C./0.2 mbar; [α]$_D^{25}$:+14.3 (c=1.1, CH$_2$Cl$_2$)
3-Hydroxypentanecarboxylic acid methyl ester: LIPODEX A, 50 m, 55° C.
$^1$H-NMR (CDCl$_3$): 0.91 (3H, t, CH$_3$—CH$_2$, 3J=7.5 Hz), 1.46 (m, 2H, CH$_2$—CH$_3$), 2.36 (1H, dd, H$_a$—CH$_2$—COOCH$_3$, 1J=16.2 Hz, 3J=8.8 Hz); 2.46 (1H, dd, H$_b$—CH$_2$—COOCH$_3$, 1J=16.2 Hz, 3J=3.2 Hz), 2.90 (1H, s, OH), 3.66 (3H, s, OCH$_3$), 3.99 (2H, m, CH—OH); $^{13}$C-NMR (CDCl$_3$): 9.7 (CH$_3$—CH$_2$), 29.3 (CH$_2$—CH$_3$), 40.7 (CH$_2$—COOCH$_3$), 51.6 (OCH$_3$), 69.2 (CH—OH), 173.4 (COOCH$_3$);
3-Hydroxybutanecarboxylic acid methyl ester: LIPODEX A, 50 m, 55° C.
$^1$H-NMR (CDCl$_3$): 1.18 (3H, d, CH$_3$—CH, 3J=6.4 Hz), 2.39 (1H, dd, H$_a$—CH$_2$—COOCH$_3$, 1J=16.2 Hz, 3J=8.3 Hz), 2.44 (1H, dd, H$_b$—CH$_2$—COOCH$_3$, 1J=16.2 Hz, 3J=3.8 Hz), 2.99 (1H, s, OH), 3.66 (3H, s, OCH$_3$), 4.15 (2H, m, CH—OH); $^{13}$C-NMR (CDCl$_3$): 22.4 (CH$_3$—CH), 42.5 (CH$_2$—COOCH$_3$), 51.6 (OCH$_3$), 64.1 (CH—OH), 173.2 (COOCH$_3$);
3-Hydroxybutanecarboxylic acid ethyl ester: LIPODEX A, 50 m, 50° C. $^1$H-NMR (CDCl$_3$): 1.18 (3H, d, CH$_3$—CH, 3J=6.2 Hz), 1.23 (3H, t, CH$_3$—CH$_2$, 3J=7.2 Hz), 2.39 (1H, dd, H$_a$—CH$_2$—COOCH$_3$, 1J=16.2 Hz, 3J=8.5 Hz), 2.43 (1H, dd, H$_b$—CH$_2$—COOCH$_3$, 1J=16.2 Hz, 3J=3.8 Hz), 2.91 (1H, s, OH), 4.13 (2H, q, CH$_2$—CH$_3$, 3J=7.2 Hz), 4.16 (2H, m, CH—OH); $^{13}$C-NMR (CDCl$_3$): 14.1 (CH$_3$—CH$_2$), 22.4 (CH$_3$—CH), 42.7 (CH$_2$—COOCH$_3$), 60.6 (OCH$_2$), 64.2 (CH—OH), 172.8 (COOCH$_3$)

LITERATURE REFERENCES

1 E.J. Corey; P.B. Hopkins *Tetrahedron Lett.* 23 (1982) 1979–1982;
2 M. Marzi; D. Misiti *Tetrahedron Lett.* 30 (1989) 6075–6076;
3 A. Haines *Carbohydrate Res.* 1 (1965) 214–228;
4 N. Machinaga; C. Kibayashi *J. Org. Chem.* 57 (1992) 5178–5189;
5 M. Marzi; P. Minetti; D. Misiti *Tetrahedron* 48 (1992) 10127–10132.

We claim:

1. A process for preparing an enantiomerically pure β-hydroxy ester by reacting a β-keto ester with hydrogen in the presence of a catalyst of the formula LRuX$_2$ where X is halogen, acetate, allyl, methallyl, 2-phenylallyl, perchlorate, trifluoroacetate, tetrafluoroborate, hexafluoroantimonate, hexafluorophosphate, hexafluoroarsenate, trichloroacetate, L is a bidentate phospholane of the formula I

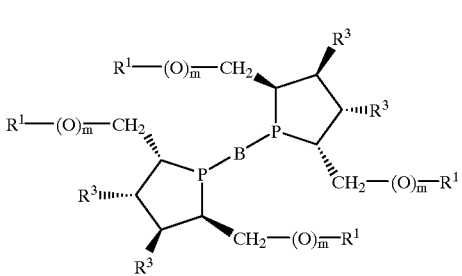

where B=a bridging link with 1–5 carbon atoms between the two phosphorus atoms,
R$^1$=H, C$_1$–C$_6$-alkyl, aryl, alkylaryl or SiR$^2{}_3$,
R$^2$=alkyl or aryl,
m=[0 or] 1,
R$^3$=H [or OR$^4$,] and
R$^4$=R$^1$.

2. A process as claimed in claim 1, wherein the reaction is conducted at a temperature between 0 and 100° C.

3. A process as claimed in claim 1, wherein the reaction is conducted at a hydrogen pressure of from 0 to 100 bar.

4. A process as claimed in claim 1, wherein the reaction takes place in a solvent which comprises alkanol.

5. A process as claimed in claim 4, wherein the solvent used is the alkanol on which the β-keto ester is based.

6. A process as claimed in claim 1, wherein the catalyst is employed in a weight ratio of from 1:10 to 1:1,000,000, based on the keto ester.

7. A process as claimed in claim 1, wherein the reaction takes place in the presence of an acid.

8. A process as claimed in claim 1, wherein the β-keto ester employed is a compound of the formula II

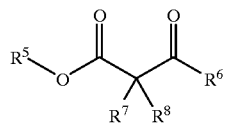

II where
- $R^5$, $R^6$=alkyl, aryl or alkylaryl, substituted or unsubstituted, and
- $R^7$, $R^8$=H, alkyl, aryl or alkoxy, substituted or unsubstituted.

9. A process as claimed in claim 8, wherein $R^6$=—$CH_2$—$CH_2$—$CH_2$—$CH_2$—$COOR^5$ and $R^7$ and $R^8$=H.

* * * * *

UNITED STATES PATENT AND TRADEMARK OFFICE
CERTIFICATE OF CORRECTION

PATENT NO. : 6,359,165 B1
DATED : March 19, 2002
INVENTOR(S) : Stürmer et al.

It is certified that error appears in the above-identified patent and that said Letters Patent is hereby corrected as shown below:

<u>Title page,</u>
ABSTRACT,
Line 4, after the formula: "$SiR_{23}$" should be -- $SiR^2_3$ --.

Signed and Sealed this

Twenty-seventh Day of August, 2002

*Attest:*

*Attesting Officer*

JAMES E. ROGAN
*Director of the United States Patent and Trademark Office*